(12) United States Patent
Igarashi et al.

(10) Patent No.: US 8,778,691 B2
(45) Date of Patent: Jul. 15, 2014

(54) BROMATE ION MEASUREMENT METHOD

(75) Inventors: Shukuro Igarashi, Ibaraki (JP); Jun Kato, Ibaraki (JP); Yoshiharu Tanaka, Tokyo (JP)

(73) Assignees: Meta Water Co., Ltd., Tokyo (JP); Ibaraki University, Ibaraki (JP)

( * ) Notice: Subject to any disclaimer, the term of this patent is extended or adjusted under 35 U.S.C. 154(b) by 0 days.

(21) Appl. No.: 13/606,459

(22) Filed: Sep. 7, 2012

(65) Prior Publication Data

US 2012/0329165 A1 Dec. 27, 2012

Related U.S. Application Data

(62) Division of application No. 12/677,146, filed as application No. PCT/JP2009/055238 on Mar. 18, 2009, now abandoned.

(30) Foreign Application Priority Data

Mar. 19, 2008 (JP) ................. 2008-070512

(51) Int. Cl.
*G01N 21/64* (2006.01)
(52) U.S. Cl.
USPC ............ 436/101; 436/124; 436/125; 436/172
(58) Field of Classification Search
USPC ................................................ 436/124, 125
See application file for complete search history.

(56) References Cited

FOREIGN PATENT DOCUMENTS

JP 09-119925 5/1997

OTHER PUBLICATIONS

Isawa, M.; Yamane T. "Simple and Rapid Determination of Trace Bromate by Flow Injection Analysis with Novel Spectrophotometric Detection System," Bunseki Kagaku, vol. 56, No. 9, Sep. 2007, 745-750.*
Gong G. et al. "A Fluorescence Quenching Mehtod for the Determination of Bromate Ion with 4,5-Dibromophenylfluorone and Cetyltrimethylammonium Bromide," Analytical Letters, 26(10), 2277-2282 (1993).*
Ferrell, S. et al. "Spectrophotometric determination of bromate ions using phenothiazines," Analytica Chimica Acta 1995, 313, 121-129.*
Mellinger, T. J. et al. "Spectrofluorometric Identification of Phenothiazine Drugs," Analytical Chemistry 1963, 35, 554-558.*
Gahr et al. "Fluorimetric Determination of Bromate by Ion-Exchange Separation and Post-Column Derivatization", *Mikrochim. Acta* 129:281-290 (1998).
Butler et al. "Bromate analysis in groundwater and wastewater samples", *J. Environ. Monit.* 7:999-1006 (2005).
Farrell et al. "Spectrophotometric determination of bromate ions using phenothiazines", *Analytica Chimica Acta* 31:121-129 (1995).

(Continued)

*Primary Examiner* — Yelena G Gakh
*Assistant Examiner* — Michelle Adams
(74) *Attorney, Agent, or Firm* — Myers Bigel Sibley & Sajovec, P.A.

(57) ABSTRACT

A method for measuring bromate ion is provided that provides high-sensitivity measurement results more simply and more quickly than conventional bromate ion measurement methods. A fluorescent substance that is quenched by coexistence with bromate ions is added to a sample 130 and the fluorescence intensity of the fluorescent substance after quenching is measured, the measured fluorescence intensity being subtracted from the fluorescence intensity of a standard sample containing no bromate ions to calculated the fluorescence intensity difference. The bromate ion concentration is calculated from the calculated fluorescence intensity difference, using a pre-determined calibration line between the fluorescence intensity difference and the bromate ion concentration.

7 Claims, 7 Drawing Sheets

(56) References Cited

OTHER PUBLICATIONS

Gowda et al, "*N*-Substituted Phenothiazines as Redox Indicators in Bromatometry", *Talanta* 26(3):233-235 (1979).

Kato et al. "Toorifuruoperajin no Keiko Shoko Gensho o Riyo shita sub- μg L-1 Level no Shusosan Ion no Teiryo", *The Japan Society for Analytical Chemistry Dai* p. 331 (2008).

Uraisin et al. "Novel oxidation reaction of prochlorperazine with bormate in the presence of synergistic activators and its application to trace determination by flow injection/spectrophotometric method", *Analytica Chimica Acta* 580:68-74 (2006).

International Search Report corresponding to International Application No. PCT/JP2009/055238 mailed May 12, 2009.

\* cited by examiner

FIG.1

← : PATH OF GENERATION BY DIRECT $O_3$ REACTION
⇐ : PATH OF GENERATION BY INDIRECT OH RADICAL REACTION

BROMATE ION MEASUREMENT METHOD

RELATED APPLICATIONS

This application is a divisional application of U.S. application Ser. No. 12/677,146, filed on Mar. 9, 2010 now abandoned, which is a U.S. national phase application of PCT International Application No. PCT/JP2009/055238, filed Mar. 18, 2009, which claims priority from Japanese Patent Application No. 2008-070512, filed Mar. 19, 2008, the disclosures of which are incorporated by reference herein in their entireties.

FIELD OF THE INVENTION

The present invention relates to a method and to an apparatus for measurement of bromate ions in water. More specifically, the present invention relates to a method and to an apparatus that can simply, quickly, and with high accuracy, measure minute amounts of bromate ions generated by ozone treatment in high standards purification of water.

BACKGROUND OF THE INVENTION

Figure 1:
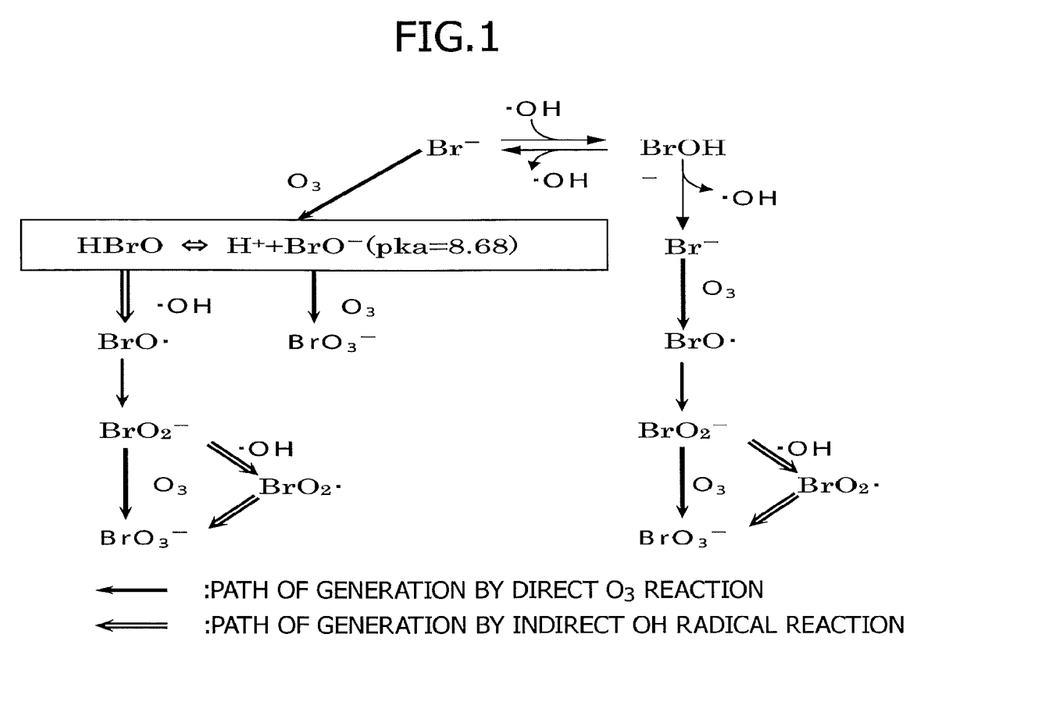
FIG. 1 Drawing showing the mechanism of generation of bromate ions by ozonification.

Water sources, such as river water, contain minute amounts of bromide ions, and when ozone treatment (water purification treatment to high standards) is performed, the bromide ions in the water react with ozone, and a reaction such as shown in FIG. 1 occurs, thereby generating bromate ions.

Bromate ions are considered to be carcinogenic and having genotoxicity, the WHO (World Health Organization) has set guideline values for the concentration thereof in drinking water at 0.01 mg/L, and in Japan as well, as of May 30, 2003, an amendment by ministry order was effected that sets the water quality standard value at 0.01 mg/L.

An analytical method generally used for analyzing bromate ions is the ion chromatograph post-column absorption intensity method. This analytical method is one in which bromate ions in a water sample are separated using a cation exchange column, sulfuric acid and an admixture of sodium nitrate and potassium bromide being added to the solution to convert the bromate ions into tribromine ions, and the tribromine ion method being used to measure the ultraviolet region absorption so as to perform quantitative determination. After the bromate ions are separated using chromatographic separation, the post column derivitization method by means of the tribromine ion method is used to measure the level of absorption of the 268 nm ultraviolet line.

In the ion chromatograph post-column (IC-PC) method, a two-stage reaction occurs: in the first reaction stage, bromate is converted by a potassium bromide/sulfuric acid solution to tribromine ions, and then in the second reaction, a sodium bromide solution is used to establish the linearity of the calibration line in the low-concentration region.

$BrO_3^- + 5Br^- + 6H^+ \rightarrow 3Br_2 + 3H_2O$ $Br_2 + Br^- + Br_3^-$

In the past, the color comparison method, the absorption intensity method, the gas chromatography method, and the ion chromatography method and the like have been used as methods for measuring bromate ions. With these methods, however, there were problems regarding sensitivity and interference by coexisting components, and it was difficult to make reliable determinations of bromate ions not exceeding 0.01 mg/L. In contrast, in Patent Reference 1, there is language describing art by which a reducing agent is added to a reagent, the reagent to which the reducing agent was added being used to determine minute quantities of ions in the liquid under measurement. Also, in Non-Patent Reference 1, there is language describing an absorption intensity method that uses a 1-cm cell, and in Non-Patent Reference 2, there is language describing an absorption intensity method that uses a 10-cm cell.

With the methods of measuring bromate ions of the past, there were problems of a complex apparatus configuration and the need for a large amount of time for the derivitization to tribromine ions.

Given the above, the present invention has as an object to provide a method and an apparatus for bromate ion measurement that can more quickly and simply perform and obtain higher-sensitivity measurement results than with conventional bromate ion measurement methods.

SUMMARY OF THE INVENTION

To achieve the above-noted object, the method for measuring bromate ions according to the present invention includes a step of mixing a fluorescent substance that is quenched by coexistence with bromate ions under acidic conditions with a sample; a step of measuring the florescence intensity after the quenching of the fluorescent substance; a step of subtracting the measured fluorescence intensity from the fluorescence intensity of a standard sample that does not contain bromate ions to calculate the fluorescence intensity difference; a step of using a pre-determined calibration line between the fluorescence intensity difference and the bromate ion concentration to calculate the bromate ion concentration from the calculated fluorescence intensity difference; and a step of determining the bromate ion concentration in the sample by measuring the fluorescence intensity after quenching of the fluorescent substance.

The method for measuring the bromate ions according to the present invention may have a step of adding a chelating agent to the sample before the step of mixing the fluorescent substance and the sample. The fluorescent substance used in the method of measuring bromate ions according to the present invention is most preferably trifluoperazine, and the chelating agent used in the method for measuring bromate ions according to the present invention may be ethylene diamine tetraacetate.

Additionally, another embodiment of the present invention is an apparatus for measuring the bromate ions included in a sample, comprising means for mixing a fluorescent substance that is quenched by coexistence with bromate ions under acidic conditions with the sample; means for measuring the fluorescence intensity after the quenching of the fluorescent substance; means for subtracting the measured fluorescence intensity from the fluorescence intensity of a standard sample that does not contain bromate ions to calculate the fluorescence intensity difference; and means for using a pre-determined calibration line between the fluorescence intensity difference and the bromate ion concentration to calculate the bromate ion concentration from the calculated fluorescence intensity.

The apparatus for measuring bromate ions according to the present invention may be constituted so as to measure with the fluorescence intensity measuring means the admixture of the sample and the fluorescent substance that is temporarily held in the mixing means.

The apparatus for measuring bromate ions according to the present invention may be constituted so as to measure with the fluorescence intensity measuring means the admixture of the sample and the fluorescent substance that flows continuously in the mixing means.

As described in detail below, the method for measuring bromate ions according to the present invention can simply and quickly provide high-sensitivity bromate ion concentration measurement results. Also, by adding a chelating agent as a metallic ion masking agent, it is possible to obtain high-sensitivity bromate ion concentration measurement results, regardless of a metallic ion included in the sample.

DESCRIPTION OF THE EMBODIMENTS OF THE PRESENT INVENTION

One aspect of a bromate ion measurement method according to the claims is described below. The present invention is not restricted to the aspect thereof described below.

Figure 13:
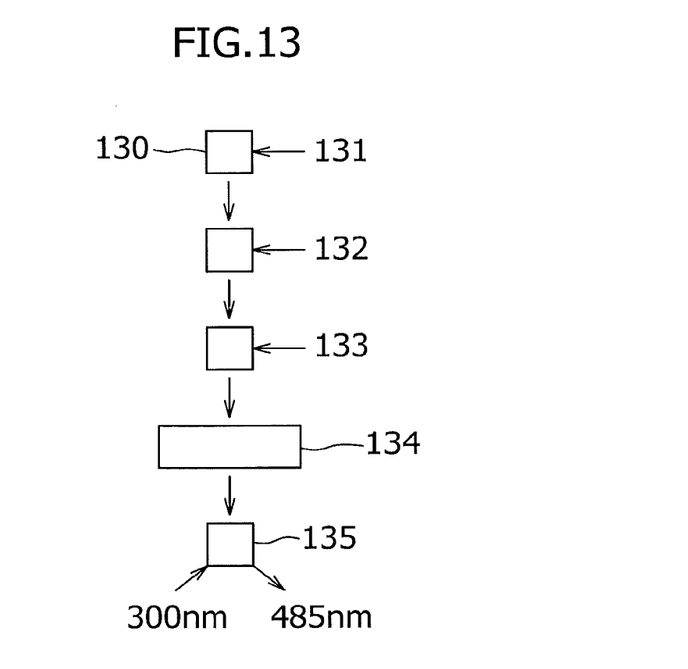
FIG. 13 Simplified flowchart of an apparatus having a batch-type configuration for the purpose of measuring the bromate ions according to the present invention.

The measurement of bromate ions in the present invention will be described, with reference made to FIG. 13. First, a sample 130 for which the bromate ion concentration is to be measured is prepared. It is preferable that a chelating agent 131 be added to the sample 130 for the purpose of masking coexisting metallic ions. The sample is mixed with a fluorescent substance 132 that is extinguished by coexistence with bromate ions in the presence of acidity. After mixing, by making the pH of the sample acidic by the addition of an acid solution 133, the fluorescent substance 132 is extinguished with dependency on the concentration of bromate ions included in the sample. The bromate ion measurement method of the present invention makes use of the property of the fluorescent substance 132 that it is extinguished by the coexistence with bromate ions in the presence of acidity, and by measuring the fluorescence intensity after extinguishing using the fluorescence intensity measuring means, it is possible to determine the bromate ion concentration included in the sample from the priorly determined relationship between fluorescence intensity and bromate ions.

Also, in the present invention it is possible to measure the fluorescence intensity by aging 134 over approximately 2 minutes from acidifying the sample by the addition of an acid solution 133, and it is possible to quickly perform the steps from taking the sample through the determination of the bromate ion concentration included in the sample. Therefore, according to the bromate ion concentration measurement method of the present invention, it is possible to quickly measure the bromate ion concentration in units of 0.001 mg/L, without the need for complex process steps or equipment.

Also, even if there is inclusion of metallic ions in the sample that represent noise in the fluorescence intensity measurement, and particularly if $Fe^{2+}$, $Fe^{3+}$, and $Mn^{2+}$ are included, by adding the chelating agent 131 to the sample for the purpose of masking the metallic ions before the fluorescent substance mixing, the tolerable limit of coexisting metallic ions becomes large, and it is possible to measure the bromate ion concentration in the same manner, with high sensitivity.

It is sufficient that the fluorescent substance 132 used in the present invention be a fluorescent substance having the property of being extinguished by coexistence with bromate ions in the presence of acidity, for example, phenothiazine derivatives such as phenothiazine, chlorpromazine, and methyl blue or the like. Of these, trifluoperazine (TFP) is the most preferable as the fluorescent substance used in the present invention.

Trifluoperazine has phenothiazine in the basic molecular structure, and it has been reported that it is dimerized by oxidation (P. Hanson, R. O. C. Norman, J. Chem. Soc. Perkin Trans. 2, 264-271 (1973)). In trifluoperazine as well, there is thought to be the same type of reaction mechanism by oxidation by bromate ions in accordance with the equations given below, and it is thought that the extinguishing phenomenon occurs in the fluorescence at a particular fluorescence wavelength and excitation wavelength, by trifluoperazine causing a change in the structure.

[Chemical Equation 1]

trifluoroperazine
fluorescence
(EX: 300 nm, EM: 485 nm)

-continued

[Chemical Equation 2]

no fluorescence
(EX: 300 nm, EM: 485 nm)

The samples that can be measured by the present invention include sedimentation processed water and filtered water in the water purification process that contain minute amounts of bromate ions.

An acid solution 133 is used for the purpose of adjusting the sample to acidity in the present invention, and hydrochloric acid is the most preferable as the acid solution.

It is sufficient that the chelating agent 131 used in the present invention be capable of masking metallic ions coexisting in the sample, and it is preferable that this be ethylene diamine tetraacetate.

Figure 10:
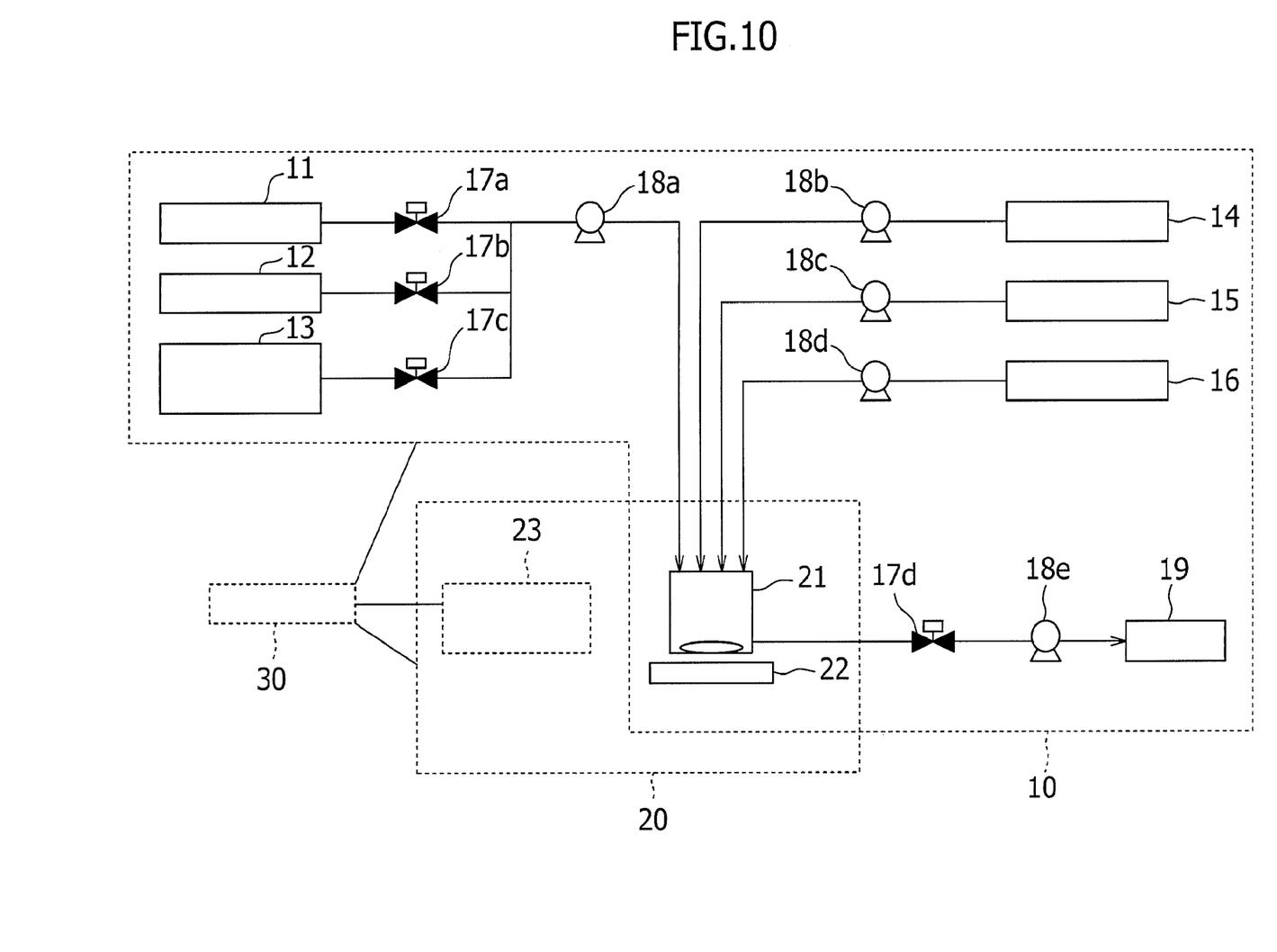
FIG. 10 Simplified schematic representation of an apparatus having a batch-type configuration for the purpose of performing measurement of bromate ions according to the present invention.

FIG. 10 shows a simplified schematic drawing of an apparatus having a batch-type configuration. As shown in FIG. 10, a batch-type measurement apparatus for bromate ions according to the present invention is formed by a liquid feed system 10 formed by sample supplying means 11, pure water supplying means 12, standard bromate ion sample supplying means 13, chelating agent supplying means 14, fluorescent substance supplying means 15, acid solution supplying means 16, a mixing cell 21, a starter 22, an effluent holding means 19, a valve 17, and a valve 18, a constant temperature chamber 20, a fluorescence intensity measurement means 23, and a control section 30 that controls the fluorescence intensity measurement means 23.

It is possible to hold the sample to be measured for bromate ion concentration in the sample supplying means 11, and it is possible to feed a prescribed amount of sample to the mixing cell 21 or the reaction coil 24.

It is possible for the pure water supplying means 12 to store pure water used as the standard sample (blank) that does not contain bromate ions for the purpose of calculating the calibration line, and it is possible to use it to supply a prescribed amount thereof to the mixing cell 21 or the reaction coil 24 as appropriate. Also, a prescribed amount of the pure water supplied by the pure water supplying means 12 may also be used for cleaning after sample measurement.

The standard bromate ion sample supplying means 13 can hold a standard sample that does not contain bromate ions for the purpose of calculating the calibration line, and can be used to supply a prescribed amount of the standard bromate ion sample to the mixing cell 21 or the coil 24 as appropriate.

The chelating agent supplying means 14, the fluorescent substance supplying means 15, and the acid solution supplying means 16 can respectively be used to hold chelating agent, a fluorescent substance, and an acid solution, and it is sufficient that a pump supply the chelating agent, the fluorescent substance, and the acid solution to the mixing cell 21 or the reaction coil 24. Also, the fluorescent substance supplying means 15 desirably has a configuration that enables complete light blockage, for the purpose of preventing quenching of the fluorescent substance.

It is sufficient that a mixing cell 21 that is usable in a batch-type configuration be capable of mixing the sample, and the chelating agent, the fluorescent substance, and the acid solution supplied by each of the above-noted supplying means, and it is preferable that it have a high permeability, and be very usable under acidic conditions. It is possible to use a quartz cell, for example, as the mixing cell 21. Also, there is a stirrer 22 installed at the bottom of the mixing cell 21, and the stirrer 2 can mix the sample and the like within the mixing cell 21.

It is sufficient that the stirrer be capable of stirring the sample or the like within the mixing cell 21, and this can be, for example, a magnetic stirrer or an ultrasonic stirrer or the like, as known in the conventional art. It is preferable that the mixing cell 21 be provided with a rotor to enable stirring by means of the stirrer 22. A sample that is stirred and mixed with a chelating agent, a fluorescent substance, and an acid solution by the stirrer 22 is measured for fluorescence intensity of the fluorescent substance by the fluorescence intensity measurement means 23.

The sample after fluorescence intensity measurement is fed as effluent to the effluent holding means 19. It is sufficient that the effluent holding means 19 be capable of temporarily holding effluent from the mixing cell 21 after measurement which is to be disposed of.

It is sufficient that the fluorescence intensity measurement means 23 be capable of measuring the intensity of fluorescence emitted by the fluorescent substance by the application of excitation light to the fluorescent substance in the sample.

The constant temperature chamber 20 can control the temperature of the mixing cell 21, the stirrer 22, the fluorescence intensity measurement means 23, and the reaction coil 24, and can control the temperature of the sample for which the fluorescence intensity is to be measured. The range of temperature controlled by the constant temperature chamber 20 is preferably no greater than 25° C. and more preferably 5° C. to 15° C.

The control section 30 can oversee control of the opening and closing of valves that control the supply samples and the like from each supplying means, control of the stirring within the mixing cell 21 by the stirrer 22, temperature control of the constant temperature chamber 20, and control of the fluorescence intensity measurement means. Also, the control section 30 calculates the measured fluorescence intensity from the fluorescence intensity of the standard sample that does not include bromate ions, performs the step of calculating the fluorescence intensity difference, and uses the calibration line determined beforehand between the fluorescence intensity difference and the bromate ion concentration to perform the step of calculating the bromate ion concentration from the calculated fluorescence intensity difference.

According to the above-noted batch-type bromate ion measurement apparatus, the sample for which the bromate ion concentration is to be measured is first prepared in the sample supplying means 11. Next, the valve 17a and pump 18a are controlled so as to supply the sample to the mixing cell 21. When this is done, in the case of supplying pure water or a standard bromate ion sample to the mixing cell 21, by controlling each of the pumps 17b and 17c, supply is possible to the mixing cell 21. Next, the chelating agent is supplied to the mixing cell 21 by the chelating agent supplying means 14. After that, the fluorescent substance is supplied to the mixing cell 21 by the fluorescent substance supplying means 15. After supplying the fluorescent substance, the acid solution is supplied to the mixing cell 21 by the acid solution supplying means 16. In the mixing cell 21, the stirrer 22 stirs the sample, the chelating agent, the fluorescent substance, and the acid solution. When this is done, the temperature within the mixing cell 21 is controlled. After mixing of the sample, the fluorescence intensity measurement means 23 measures the intensity of the fluorescence emitted from the fluorescent substance in the sample. After measurement of the fluorescence intensity, in the control section 30b, the fluorescence intensity difference is calculated by subtracting the measured fluorescence intensity from the fluorescence intensity of the standard sample that does not include bromate ions. Next, using the pre-determined calibration line between the fluorescence intensity difference and the bromate ion concentration, the bromate ion concentration is calculated from the fluorescence intensity difference. After the fluorescence intensity measurement, the sample is sent as effluent to a means that receives the sample. The supply of the sample and the chelating agent can be done by control of the valves 17a-c and pumps 18a-d by the controller section 30. In the same manner, the processing of the effluent from the mixing cell 21 can be controlled by the control section 30 controlling the valve 17d and the pump 18e.

Figure 12:
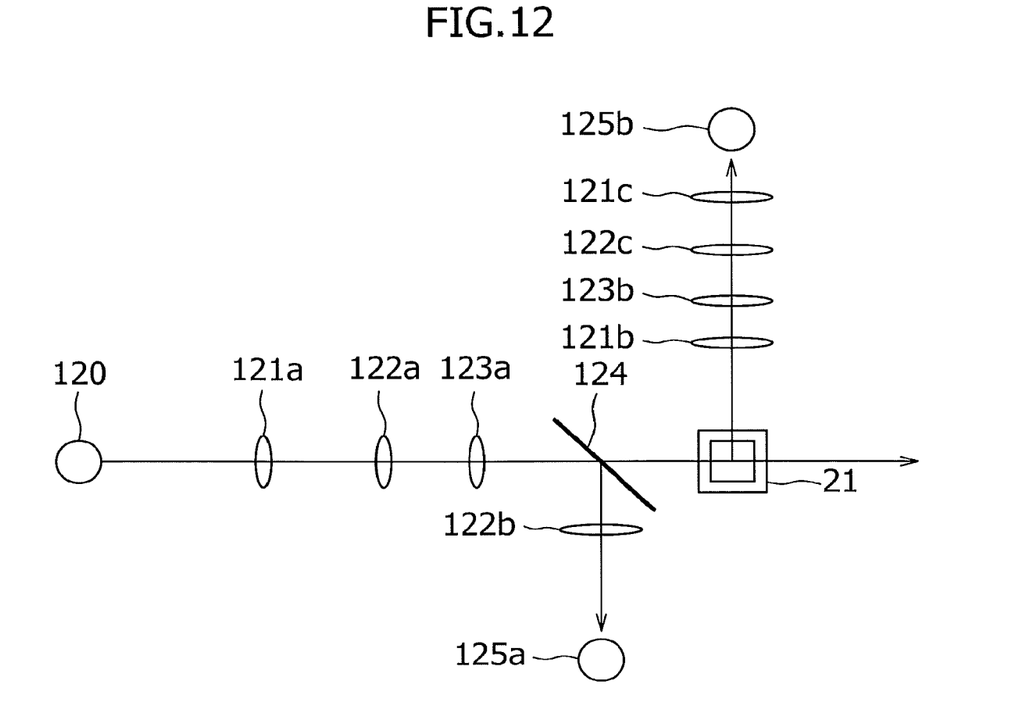
FIG. 12 Simplified schematic representation of means for measuring fluorescence intensity for the purpose of performing measurement of bromate ions according to the present invention.

Next, FIG. 12 shows an aspect of a fluorescence intensity measurement means 23 of the present invention. As shown in FIG. 12, the fluorescence intensity measurement means 23 is formed by an excitation light source 120, collimator lenses 121a-c, slits 122a-c, bandpass filters (BPFs) 123a, b, a beam splitter 124, photomultiplier tubes (PMTs) 125a, b, and the mixing cell 21.

It is sufficient that excitation light source 120 be capable of emitting a source of light to strike the fluorescent substance of the sample in the mixing cell 21 or a flow cell, and this can be a xenon lamp, a mercury xenon lamp, or a halogen lamp or the like.

The collimator lens 121a can collimate the scattered light from the excitation light source 120 in the direction of the mixed sample. The collimator lens 121b can collimate the wavelength emitted from the fluorescent substance within the mixed sample in the direction of the PMT 123b for measuring fluorescence. Also, the collimating lens 121c can collimate a wavelength that is emitted from the fluorescent substance and passes through the BPM 123b to the measurement position of the PMT 125b for measuring the fluorescence. Conventional known lenses can be used as such collimator lenses.

The slit 122 constricts the light collimated by the collimator lens from the excitation light source. As long as this configuration is adopted, it is possible to use a conventional known slit.

The bandpass filter (BPM) 123a can block a particular wavelength, and send a particular wavelength to the mixed sample. The BPM 123b, in the same manner, can block a particular wavelength and send a particular wavelength only to the PMT 125b. It is preferable that, as a bandpass filter, a filter that passes only a wavelength of 300 nm or 480 nm be used, and it is possible for this to be a known conventional type.

It is sufficient that the beam splitter 124 be capable of splitting into two the incident light, and this can be a known conventional type.

The photomultiplier tube (PMT) 125a can measure the temporal variations with regard to the amount of light from the excitation light source, and it is possible to use this measured value for correction at the time the fluorescence intensity is calculated. Also, the PMT 125b measures the amount of light at the wavelength emitted from the fluorescent substance within the sample. It is possible to use a known conventional type of PMT.

According to the fluorescence intensity measurement means 23 shown in FIG. 12, scattered light emitted from the excitation light source 120 is collimated by the collimator lens 121a, passes through the slit 122a, and enters the BPM 123a. The BPM 123a passes only the wavelength of 300 nm, and sends the wavelength of 300 nm to the beam splitter 124. At the beam splitter 124 one of the two split wavelengths passes through the slit 122b, and is sent to the PMT 125a. At the PMT 125a, in order to perform correction at the time of measurement of the fluorescence intensity, the temporal variations in the amount of light from the excitation light source 120 are measured. The other wavelength that passes through the beam splitter 124 enters the mixing cell 21, and excites the fluorescent substance. The wavelength emitted from the excited fluorescent substance is collimated by the collimator lens 121b and enters the BPM 123b. The BPM 123b blocks wavelengths other than 480 nm, and sends the 480-nm wavelength to the slit 122c. The wavelength that passes through the slit 122c is once again collimated to the position of the PMT 125b that measures the fluorescence intensity. The PMT 125b measures the fluorescence intensity of the wavelength emitted from the fluorescent substance.

Figure 11:
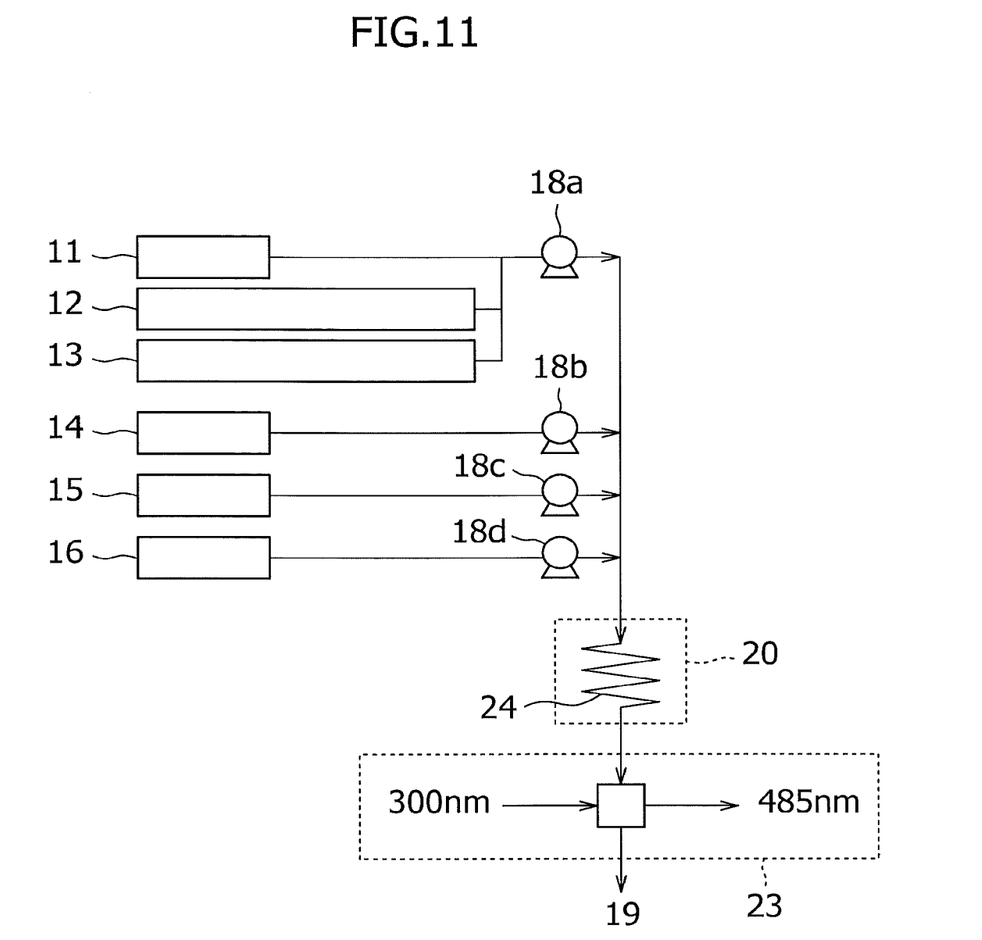
FIG. 11 Simplified schematic representation of an apparatus having a flow injection-type configuration for the purpose of performing measurement of bromate ions according to the present invention.

FIG. 11 is a simplified schematic drawing of an apparatus having a flow injection configuration for the purpose performing measurement of bromate ions according to the present invention. As shown in FIG. 11, the flow injection type measurement apparatus for bromate ions according to the present invention is formed by sample supplying means 11, the pure water supplying means 12, the bromate ion standard sample supplying means 13, the chelating agent supplying means 14, the fluorescent substance supplying means 15, the acid solution supplying means 16, the pumps 18a-d, the reaction coil 24, the constant temperature chamber 20, the fluorescent substance intensity measurement means 23, and the effluent holding means 19.

It is sufficient that the reaction coil 24 that can be used in the flow injection type configuration have a constitution that enables mixing while the sample, the chelating agent, the fluorescent substance, and the acid solution supplied by the supplying means are flowing continuously in the reaction coil 24. The length of the reaction coil 24 and the flow amount therein are preferably set appropriately such that the sample and the like are sufficiently mixed. The sample that is mixed within the reaction coil 24 has its fluorescence intensity measured by the fluorescence intensity measurement means 23.

According to the above-noted flow injection type bromate ion measurement apparatus, the sample to be measured for bromate ion concentration is prepared in the sample supplying means 11. Next the pump 18 is controlled and the sample is supplied to the reaction coil 24. When this is done, in the case in which pure water or a standard bromate ion sample is supplied to the reaction coil 24, the respective valves (not shown in the drawing) are controlled to perform supply to the reaction coil 24. Next, in the midway in the pipe that supplies the sample to the reaction coil 24, a chelating agent is supplied by the chelating agent supplying means 14. After that, in the same manner, midway in the pipe the fluorescent substance is supplied by the fluorescent substance supplying means 15. After supplying the fluorescent substance, the acid solution is further supplied to within the reaction cell by the acid solution supplying means 16. The reaction cell 24 is constituted so as to sufficiently mix the sample, the chelating agent, the fluorescent substance, and the chelating agent flowing therewithin, and the reaction coil 24 is temperature controlled by the constant temperature chamber 20. The intensity of the fluorescence emitted by the fluorescent substance within the sample that is mixed in the reaction coil 24 is measured by the fluorescent substance intensity measurement means 23, and the location measured by the fluorescence intensity measurement means 23 has a flow cell configuration so as to enable measurement of the sample flowing within the flow cell. After fluorescence intensity measurement, the sample is sent as effluent to the effluent holding means 19.

EXAMPLES

Although the present invention is further particularly illustrated below by embodiments, the present invention is not restricted to these embodiments.

Example 1

Figure 2:
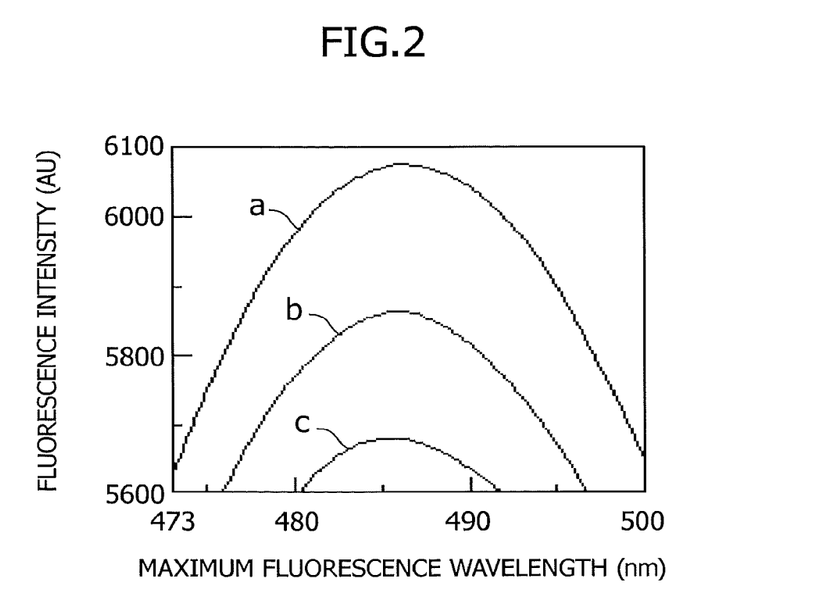
FIG. 2 Graph showing the fluorescent spectrum for different bromate ion concentrations.

The dependency of trifluoperazine fluorescence intensity on the bromate ion concentration was measured under acidic conditions. Specifically, after sequentially adding and mixing a 3.2-ml bromate ion sample solution, 0.2 ml of TFP solution, and 0.6 ml of acid solution in a sample tube, the fluorescence was measured after 2 minutes (with an excitation wavelength of 300 nm, and a fluorescence wavelength of 485 nm) using a fluorescence spectrophotometer (product name: F4500, made by Hitachi). In the bromate ion sample solution, the proportions of bromate ion concentrations were, respectively, a) blank (no bromate ion content), b) 7.5 µg/L, and c) 15 µg/L. FIG. 2 shows the fluorescence spectrum of trifluoperazine with respect to samples with various bromate ion concentrations. From these results, it was seen that a quenching phenomenon occurred due to the bromate ion. Also, it was determined that, as the bromate ion concentration increased, the quenching of the fluorescence became greater.

Example 2

Figure 3:
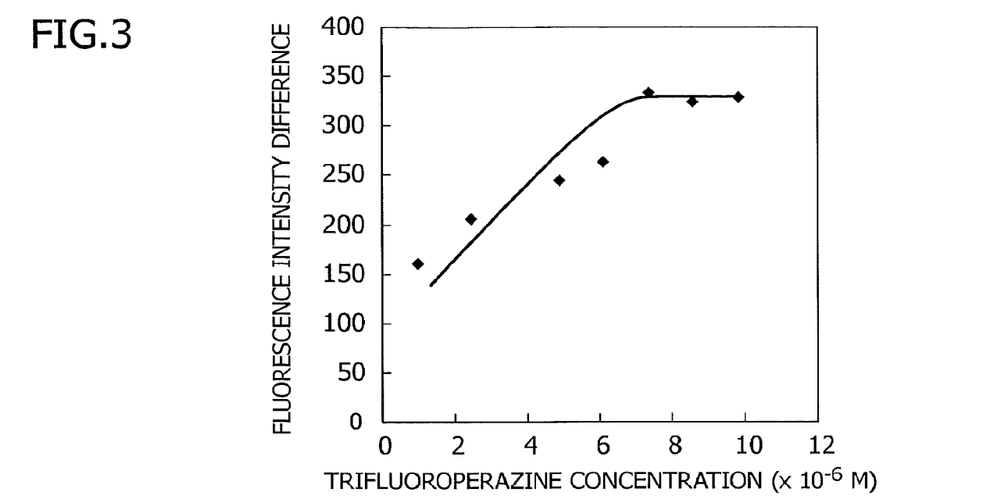
FIG. 3 Graph showing the relationship between the added trifluoperazine concentration and the fluorescence intensity difference.

An investigation was made of the trifluoperazine concentration used in the measurement method of the present invention. Using the same type of step as in Example 1, the measurement method for bromate ions was performed. An acid solution and hydrochloric acid were used, with the hydrochloric acid set to 1.0 M. Using bromate ion sample solutions, one blank and one that was 11 µg/L, the measurement was performed as the TFP concentration was varied. The fluorescence intensity differences between the solution containing bromate ions and the blank corresponding to the TFP concentrations were obtained. The results regarding the influence of the concentration of the added TFP and the thus-obtained fluorescence intensity differences (the differences between the fluorescence intensity of the blank sample and the fluorescence intensity of the sample having a bromate ion concentration of 11 µg/L) are shown in FIG. 3. The difference in fluorescence intensity between the blank and the sample containing bromate ions increased up to a trifluoperazine concentration of $7.35 \times 10^{-6}$ M, after which it was constant. From these results, it is thought that bromate ions completely react at a trifluoperazine concentration of at least $7.35 \times 10^{-6}$ M. In the following embodiments, the concentration of trifluoperazine was made $7.35 \times 10^{-6}$ M.

Example 3

Figure 4:
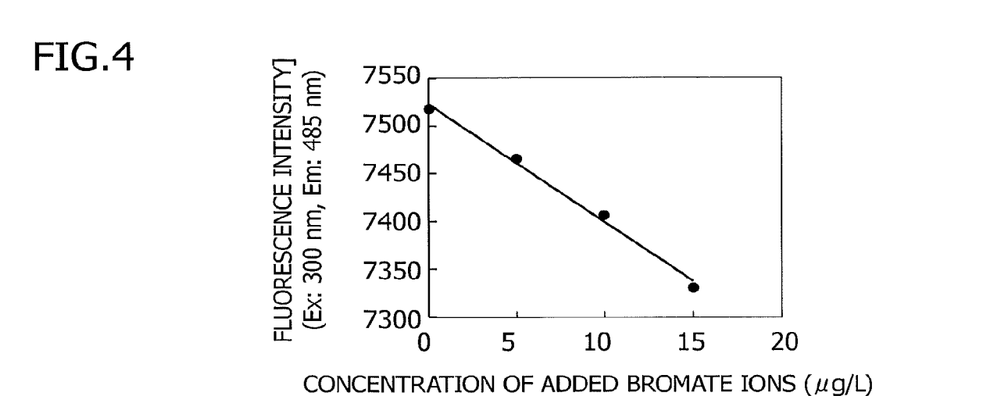
FIG. 4 Graph showing the results of measuring the bromate ion concentration when hydrochloric acid is used as the acid solution.
Figure 5:
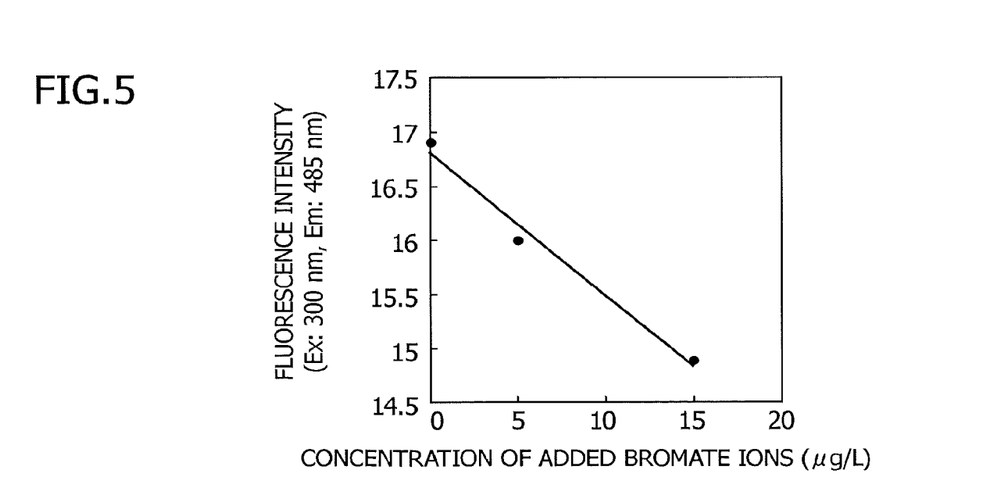
FIG. 5 Graph showing the results of measuring the bromate ion concentration when nitric acid is used as the acid solution.
Figure 6:
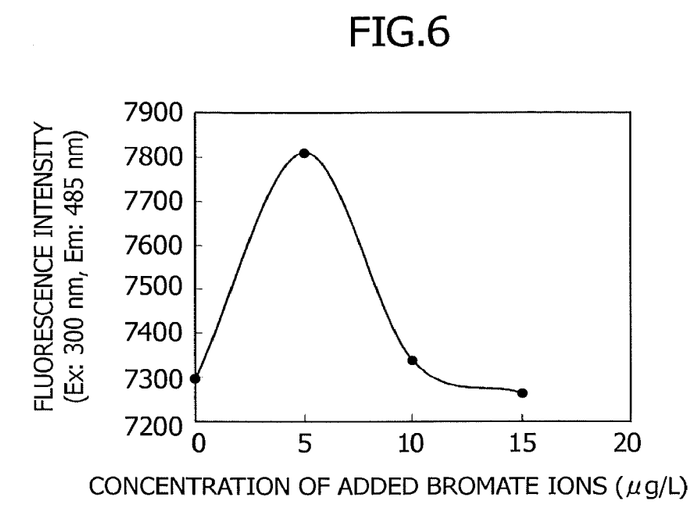
FIG. 6 Graph showing the results of measuring the bromate ion concentration when sulfuric acid is used as the acid solution.

An investigation was performed of the acid used in the bromate ion measurement method of the present invention, Using the same type of step as in Example 1, the measurement method for bromate ions was performed. When this was done, a comparison was performed by using hydrochloric acid, nitric acid, and sulfuric acid in the acid solution. Given Embodiment 2, the concentration of trifluoperazine was made $7.35 \times 10^{-6}$ M, and the bromate ion concentration was varied from 0 to 15 µg/L. In the case of using hydrochloric acid in the acid solution, addition was done to make the hydrochloric acid concentration 0.9 M ($[H^+]_T$=0.9 M and $[Cl^-]_T$=0.9 M), and the results are shown in FIG. 4. In the case of using nitric acid in the acid solution, addition was done to make the nitric acid concentration 0.9 M ($[H^+]_T$=0.9 M and $[NO_3^-]_T$=0.9 M), and the results are shown in FIG. 5. In the case of using sulfuric acid in the acid solution, addition was done to make the sulfuric acid concentration 0.45 M ($[H^+]_T$=0.9 M and $[SO_4^{2-}]_T$=0.45 M, and the results are shown in FIG. 6.

In the case of using hydrochloric acid in the acid solution, the result was a quantitative decrease in the fluorescence intensity with respect to the bromate ion concentration. In the case of using nitric acid, the fluorescence intensity was approximately ¹⁄₄₄₄ compared with the case of using hydrochloric acid. In the case of using sulfuric acid, although the same level of fluorescence intensity was obtained as with the case of using hydrochloric acid, there was no quantitative decrease in the fluorescence intensity with respect to the bromate ion concentration. From these results, therefore, it is possible to quantitatively determine the bromate ions when using hydrochloric acid as the acid solution.

Example 4

Figure 7:
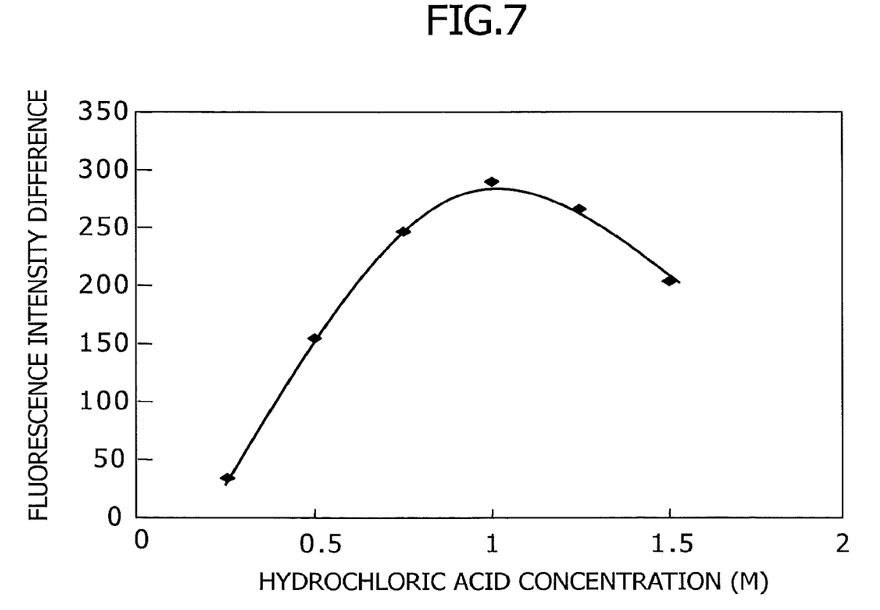
FIG. 7 Graph showing the results of measuring the relationship between the hydrochloric acid concentration and the fluorescence intensity when hydrochloric acid is used as the acid solution.

An investigation was performed on the influence of varying the hydrochloric acid concentration when hydrochloric acid is used in the acid solution. Using the same type of step as in Embodiment 1, the measurement method for bromate ions was performed. The TFP concentration was set to $7.35 \times 10^{-6}$ M, the bromate ion concentration was set to 11 µg/L, and the hydrochloric acid concentration was varied from 0.25 to 1.5 M. FIG. 7 shows the relationship between the hydrochloric acid concentration and the fluorescence intensity. Because the fluorescence intensity difference between blank and the sample was maximum at a hydrochloric acid concentration of 1.0 M, the hydrochloric acid concentration was set to 1.0 M. It is thought that the decrease in the fluorescence intensity below 1.0 M is due to insufficient acidity for the quenching reaction to occur, and it is thought that the decrease in the fluorescence intensity at about 1.0 M is due to the prevention of dimers as the reaction of emitting protons proceeds to the right side in the reaction mechanism.

[Chemical Equation 3]

no fluorescence
(EX: 300 nm, EM: 485 nm)

Example 5

Figure 8:
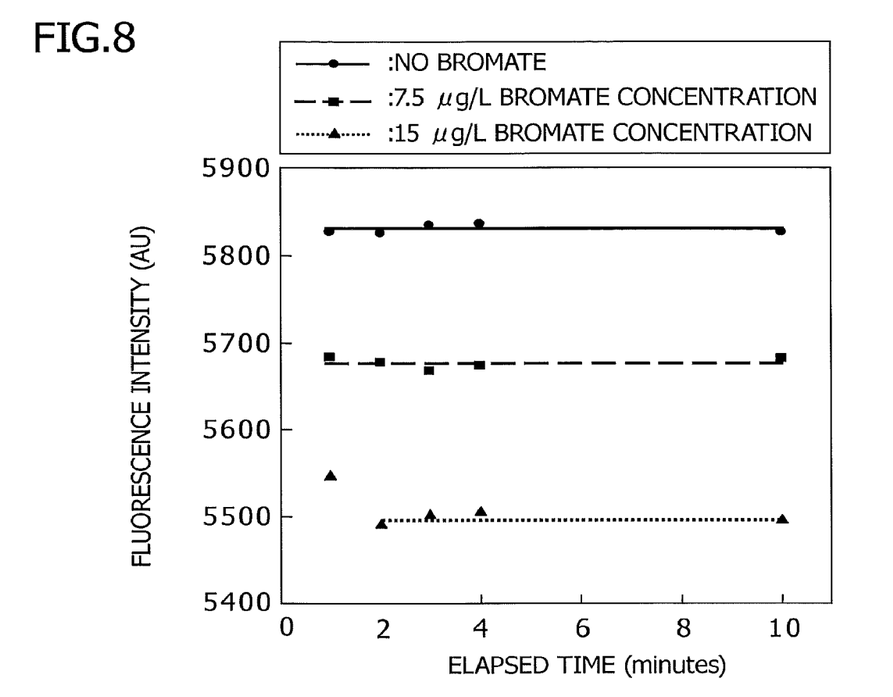
FIG. 8 Graph showing the relationship between the reaction time and different bromate ion concentrations.

An investigation was performed on the relationship of the reaction time and various bromate ion concentrations to the fluorescence intensity. Using the same type of step as in Example 1, the measurement method for bromate ions was performed. The TFP concentration was set to $7.35 \times 10^{-6}$ M, hydrochloric acid was used in the acid solution, and the hydrochloric acid concentration was set to 1.0 M. The bromate ion concentrations used were blank, 7.5 μg/L, and 15 μg/L. The reaction time from the adding of the hydrochloric acid to the sample to which the TFP solution had been added was varied and the respective fluorescence intensities at 25° C. were measured. FIG. 8 shows the relationship of the reaction time and bromate ion concentration to the fluorescence intensity. Because no change was observed after the elapse of 2 minutes of reaction time in all cases of the bromate ion concentrations of 7.5 μg/L, 15 μg/L, and blank, the reaction time was set to approximately 2 minutes. In the drawing, the reaction times are indicated with the addition of the acid solution taken as being 0 seconds.

Example 6

Figure 9:
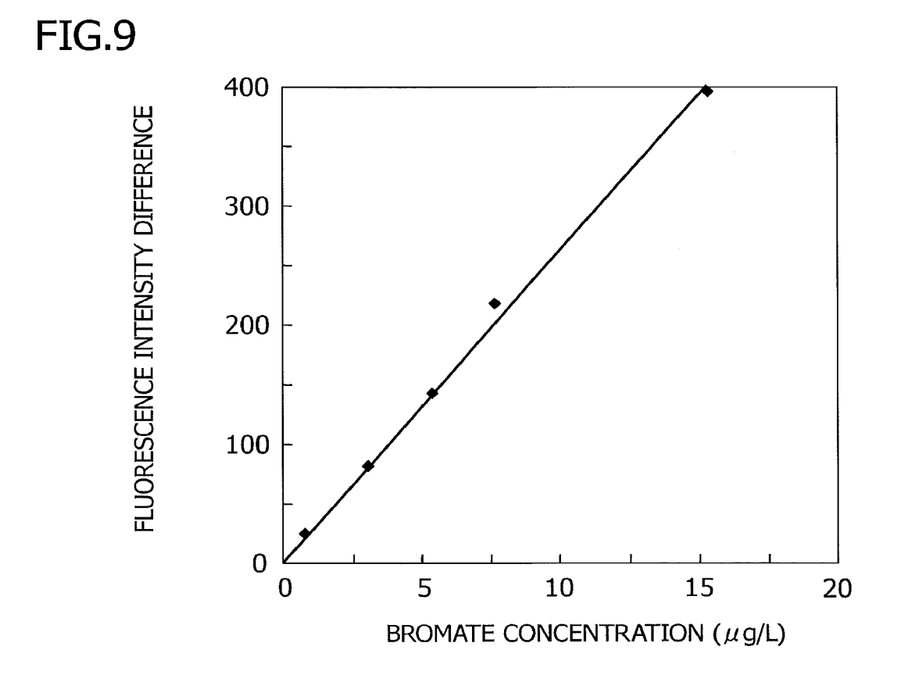
FIG. 9 Graph showing the relationship (calibration line) between the bromate ion concentration and the fluorescence intensity difference.

An investigation was performed on the dependency of fluorescence intensity on bromate ion concentration. Using the same type of step as in Example 1, the measurement method for bromate ions was performed. The TFP concentration was set to $7.35 \times 10^{-6}$ M, hydrochloric acid was used as the acid solution, and the hydrochloric acid concentration was set to 1.0 M. The bromate ion concentration in the sample was varied and the fluorescence intensity difference was measured to obtain a bromate ion calibration line. FIG. 9 shows the bromate ion concentration calibration line. The relationship between bromate ion concentration in the sample and fluorescence intensity difference obtained from this calibration line was y=26.42x (where y is the fluorescence intensity difference and x is the bromate ion concentration in μg/L), the correlation coefficient being 0.997. At a bromate ion concentration of 7.5 μg/L, the relative standard deviation with 5 measurements was 2.71%, and the detection limit (3σ) was 0.58 μg/L.

Example 7

An investigation was performed on the influence of coexisting substances on the fluorescence intensity difference with a bromate ion blank and a bromate ion concentration of 7.5 μg/L ($6.0 \times 10^{-8}$ M), and the results are shown in Table 1. The tolerable concentration limit of a coexisting substance, taken as the concentration that results in an error within ±5% in the above-noted fluorescence intensity difference, was compared by molar ratios with the bromate ion concentration. As a result, a tolerable limit for $Al^{+3}$, $Ca^{2+}$, $K^+$, $Na^+$, $Ni^{2+}$, $Mg^{2+}$, $Cl^-$, $NO_3^-$, and $SO_4^{2-}$ was ×1000, and for $Zn^{2+}$, $IO_3^-$, $IO_4^-$, and ethylene diamine tetraacetate was ×100. Also, although the tolerable limit was a low value of ×1 for $Fe^{2+}$, $Fe^{3+}$, and $Mn^{2+}$, by using ethylene diamine tetraacetate as a masking agent, it was possible to allow the tolerable limit to be ×10 for $Fe^{2+}$, $Fe^{3+}$, and $Mn^{2+}$.

TABLE 1

| Coexisting substance | Tolerable limit (within ± 5%) of molar ratio with respect to bromate ions |
|---|---|
| $Al^{3+}$, $Ca^{2+}$, $K^+$, $Na^+$, $Ni^{2+}$ $Mg^{2+}$, $Cl^-$, $NO_3^-$, $SO_4^{2-}$ | ×1000 |
| $Zn^{2+}$, $IO_3^-$, $IO_4^-$, ethylene diamine tetraacetate *$Fe^{2+}$, *$Fe^{3+}$, *$Mn^{2+}$ | ×10 |
| $Fe^{2+}$, $Fe^{3+}$, $Mn^{2+}$ | ×1 |

*Masked by [ethylene diamine tetraacetate]$_T$ = $6.0 \times 10^{-7}$M
[$BrO_3^-$]$_T$ = $6.0 \times 10^{-8}$M (7.5 μg/L)
[TFP]$_T$ = $7.35 \times 10^{-6}$M, [HCl]$_T$ = 1.0M As an application of the present method, a quantitative determination was made of the bromate ions included in the commercially available Crystal Geyser (made by CG Roxane), using the standard addition method, the result being shown in Table 2. At a bromate ion concentration of 7.5 μg/L, the relative standard deviation was 3.02%. Also, good results were obtained for the potassium bromide recovery rate, which was 96% at 7.5 μg/L and 103% at 15 μg/L.

TABLE 2

| Amount added (μg/L) | Detected value (μg/L) | Recovery rate (%) |
|---|---|---|
| Blank | N.D. | — |
| 7.5 | 7.2 | 96 |
| 15.0 | 15.5 | 103 |

A comparison of the present method with other methods is shown in Table 3. The present fluorescence intensity method, compared with the ion chromatography post-column method[1] currently adopted as a method of testing for bromate ions ("Drinking Water Testing Methods" 2001 Edition, Expanded Edition, p. 16 (2006), (Japan Water Works Association)), the absorption spectrographic method using a 1-cm cell$^2$) (Non-Patent Reference 1) and the absorption spectrographic method using a 10-cm cell$^2$) (Non-Patent Reference 2), is simpler than the former, and with respect to the latter has a 10-fold improvement in sensitivity and does not require a special cell and analytical equipment, making it more generally usable,

TABLE 3

| Method | Cell (cm) | Quantitative determination range (μg/L) | Detection limit (3σ) (μg/L) |
| --- | --- | --- | --- |
| Fluorescence intensity (trifluoperazine) | 1 | 0.8-15 | 0.58 |
| Absorption spectrography (trifluoperazine) | 10 | 1-700 | 0.67 |
| Absorption spectrography (triiodide) | 1 | 50-150 | 10 |
| Ion chromatography post column absorption spectrography (tribromide) | — | 0.5-50 | 0.19 |

That which is claimed:

1. A method for measuring bromate ions in a sample, comprising the steps of:
    mixing trifluoperazine with the sample, wherein fluorescence emission from trifluoperazine is quenched in the presence of bromate ions under acidic conditions;
    measuring florescence intensity emitted from the mixture of trifluoperazine and the sample under acidic conditions;
    subtracting the measured fluorescence intensity emitted from the mixture of trifluoperazine and the sample from a measured fluorescence intensity emitted from a standard sample that does not contain bromate ions to calculate a fluorescence intensity difference; and
    determining the bromate ion concentration in the sample from the calculated fluorescence intensity difference using a pre-determined calibration line that relates fluorescence intensity difference with bromate ion concentration,
    wherein the method further comprises a step of adding a chelating agent to the sample before the step of mixing trifluoperazine and the sample, and wherein the chelating agent is ethylene diamine tetraacetate.

2. A method for measuring bromate ions in a sample, comprising the steps of:
    mixing trifluoperazine with the sample to provide a mixture of trifluoperazine and the sample;
    adding hydrochloric acid to the mixture of trifluoperazine and the sample to provide a mixture of trifluoperazine, the sample and hydrochloric acid;
    measuring florescence intensity emitted from the mixture of trifluoperazine, the sample and hydrochloric acid;
    subtracting the measured fluorescence intensity emitted from the mixture of trifluoperazine, the sample and hydrochloric acid from a measured fluorescence intensity emitted from a standard sample that does not contain bromate ions to calculate a fluorescence intensity difference; and
    determining the bromate ion concentration in the sample from the calculated fluorescence intensity difference using a pre-determined calibration line that relates fluorescence intensity difference with bromate ion concentration.

3. The method according to claim 2, wherein the method further comprises a step of adding a chelating agent to the sample before the step of mixing trifluoperazine with the sample.

4. The method according to claim 3, wherein the chelating agent is ethylene diamine tetraacetate.

5. The method according to claim 2, wherein the mixture of trifluoperazine, the sample and hydrochloric acid has a hydrochloric acid concentration between 0.25 M and 1.5 M.

6. The method according to claim 2, wherein the mixture of trifluoperazine, the sample and hydrochloric acid has a trifluoperazine concentration of at least $7.35 \times 10^{-6}$ M.

7. The method according to claim 2, wherein fluorescence intensity is measured using an excitation wavelength of 300 nm and a fluorescence wavelength of 485 nm.

* * * * *